(12) United States Patent
Rasmussen et al.

(10) Patent No.: US 7,666,219 B2
(45) Date of Patent: *Feb. 23, 2010

(54) PROSTHESIS DEPLOYMENT SYSTEM RETENTION DEVICE

(75) Inventors: Erik E. Rasmussen, Slagelse (DK); Jens Vejby Schultz, Skovlunde (DK); Bent Øhlenschlaeger, Lille Skensved (DK)

(73) Assignee: Cook Incorporated, Bloomington, IN (US)

( * ) Notice: Subject to any disclaimer, the term of this patent is extended or adjusted under 35 U.S.C. 154(b) by 956 days.

This patent is subject to a terminal disclaimer.

(21) Appl. No.: 10/963,078

(22) Filed: Oct. 12, 2004

(65) Prior Publication Data

US 2005/0085890 A1 Apr. 21, 2005

Related U.S. Application Data

(60) Provisional application No. 60/511,608, filed on Oct. 15, 2003.

(51) Int. Cl.
*A61F 2/06* (2006.01)

(52) U.S. Cl. ..................................................... 623/1.12

(58) Field of Classification Search ....... 623/1.11–1.46; 606/191–198
See application file for complete search history.

(56) References Cited

U.S. PATENT DOCUMENTS

| | | | |
|---|---|---|---|
| 4,562,596 A | 1/1986 | Kornberg | |
| 4,665,918 A | 5/1987 | Garza et al. | |
| 4,950,227 A | 8/1990 | Savin et al. | |
| 5,387,235 A | 2/1995 | Chuter | |
| 5,720,776 A | 2/1998 | Chuter et al. | |
| 6,206,931 B1 | 3/2001 | Cook et al. | |
| 6,530,949 B2* | 3/2003 | Konya et al. | 623/1.12 |
| 6,569,193 B1* | 5/2003 | Cox et al. | 623/1.15 |
| 6,695,875 B2* | 2/2004 | Stelter et al. | 623/1.13 |
| 7,335,224 B2* | 2/2008 | Ohlenschlæger | 623/1.11 |
| 2003/0233140 A1 | 12/2003 | Hartley et al. | |
| 2004/0054396 A1 | 3/2004 | Hartley et al. | |
| 2004/0098079 A1 | 5/2004 | Hartley et al. | |

FOREIGN PATENT DOCUMENTS

| | | |
|---|---|---|
| WO | WO 98/53761 | 12/1998 |
| WO | WO 99/29262 | 6/1999 |
| WO | WO 03/034948 A1 | 5/2003 |
| WO | WO 03/053287 A1 | 7/2003 |

* cited by examiner

*Primary Examiner*—Kevin T Truong
(74) *Attorney, Agent, or Firm*—Brinks Hofer Gilson & Lione (57) ABSTRACT

An introducer for an expandable endovascular prosthesis having a self a self-expanding stent includes a proximal prosthesis positioning mechanism that has a retention device to retain the self-expanding stent and a control member to selectively release the retention device from the prosthesis. The retention device includes an opening forming a tapered cavity. The control member includes a plurality of loops coupled to the prosthesis and a trigger wire. The trigger wire passes through a first aperture of the retention device, through the plurality of loops, and through and a second aperture of the retention device to retain the loops.

20 Claims, 14 Drawing Sheets

PROSTHESIS DEPLOYMENT SYSTEM RETENTION DEVICE

CROSS-REFERENCE TO RELATED APPLICATIONS

This invention relates to and claims all benefits available from prior filed provisional application Ser. No. 60/511,608 filed Oct. 15, 2003.

BACKGROUND OF THE INVENTION

1. Technical Field

This invention relates to a medical device and, in particular, an introducer and a method for retaining and releasing an expandable, intraluminal prosthesis for the endovascular repair of a diseased or damaged vessel.

2. Related Art

Throughout this specification the terms proximal and proximally are used for a position or direction towards the patient's heart and the terms distal and distally are used for a position or direction away from the patient's heart.

The deployment of intraluminal prostheses into the lumen of a patient from a remote location by the use of a deployment device or introducer has been disclosed in a number of earlier patents and patent applications. U.S. Pat. No. 4,562,596 entitled "Aortic Graft, Device and Method for Performing an Intraluminal Abdominal Aortic Aneurysm Repair", which is incorporated herein by reference, proposes the retention of a self-expanding graft within a sleeve until it is to be deployed, at which time the sleeve is withdrawn and the graft is allowed to expand. U.S. Pat. No. 4,665,918 entitled "Prosthesis System and Method", which is incorporated herein by reference, proposes a system and method for the deployment of a prosthesis in a blood vessel. The prosthesis is positioned between a delivery catheter and an outer sheath and expands outwardly upon removal of the sheath.

U.S. Pat. No. 4,950,227 entitled "Stent Delivery System", which is incorporated herein by reference, proposes the delivery of a stent by mounting the stent to the outside of an inflatable catheter and retaining the ends of the unexpanded stent by fitting a sleeve over either end of the stent. Expansion of the stent is caused by inflation of the catheter between the sleeves so that the ends of the stent are withdrawn from the respective sleeves and the stent released and expanded into position.

U.S. Pat. No. 5,387,235 entitled "Expandable Transluminal Graft Prosthesis for Repair of Aneurysm", which is incorporated herein by reference, discloses apparatus and methods of retaining grafts onto deployment devices. These features and other features disclosed in U.S. Pat. No. 5,387,235 could be used with the present invention.

U.S. Pat. No. 5,720,776 entitled "Barb and Expandable Transluminal Graft Prosthesis for Repair of Aneurysm", which is incorporated herein by reference, discloses improved barbs with various forms of mechanical attachment to a stent. These features and other features disclosed in U.S. Pat. No. 5,720,776 could be used with the present invention.

U.S. Pat. No. 6,206,931 entitled "Graft Prosthesis Materials" discloses graft prosthesis materials and a method for implanting, transplanting replacing and repairing a part of a patient and particularly the manufacture and use of a purified, collagen based matrix structure removed from a submucosa tissue source. These features and other features disclosed in U.S. Pat. No. 6,206,931 could be used with the present invention, and the disclosure of U.S. Pat. No. 6,206,931 is incorporated herein by reference.

PCT Patent Publication Number No. WO99/29262 entitled "Endoluminal Aortic Stents" discloses a fenestrated prosthesis for placement where there are intersecting arteries. This feature and other features disclosed in PCT Patent Publication Number No. WO99/29262 could be used with the present invention, and the disclosure of PCT Patent Publication Number No. WO99/29262 is incorporated herein by reference.

PCT Patent Publication Number No. WO03/034948 entitled "Prostheses for Curved Lumens" discloses prostheses with arrangements for bending the prosthesis for placement into curved lumens. This feature and other features disclosed in PCT Patent Publication Number No. WO03/034948 could be used with the present invention, and the disclosure of PCT Patent Publication Number No. WO03/034948 is incorporated herein by reference.

U.S. Utility patent application Ser. No. 10/447,406 entitled "Trigger Wire System" discloses release wire systems for the release of stent grafts retained on introducer devices. This feature and other features disclosed in U.S. Utility patent application Ser. No. 10/447,406 could be used with the present invention, and the disclosure of U.S. Utility patent application Ser. No. 10/447,406 is incorporated herein by reference.

U.S. Utility patent application Ser. No. 10/609,846 entitled "Thoracic Aortic Stent Graft Deployment Device" discloses introducer devices adapted for deployment of stent grafts particularly in the thoracic arch. This feature and other features disclosed in U.S. Utility patent application Ser. No. 10/609,846 could be used with the present invention, and the disclosure of U.S. Utility patent application Ser. No. 10/609,846 is incorporated herein by reference.

U.S. Utility patent application Ser. No. 10/602,930 entitled "Stent-Graft Fastening" discloses arrangements for fastening stents onto grafts particularly for exposed stents. This feature and other features disclosed in U.S. Utility patent application Ser. No. 10/602,930 could be used with the present invention, and the disclosure of U.S. Utility patent application Ser. No. 10/602,930 is incorporated herein by reference.

PCT Patent Publication Number No. WO03/053287 entitled "Stent Graft with Improved Graft Adhesion" discloses arrangements on stent grafts for enhancing the adhesion of such stent grafts into walls of vessels in which they are deployed. This feature and other features disclosed in PCT Patent Publication Number No. WO03/053287 could be used with the present invention, and the disclosure of PCT Patent Publication Number No. WO03/053287 is incorporated herein by reference.

PCT Patent Publication Number No. WO98/53761 entitled "A Prosthesis and a Method and Means of Deploying a Prosthesis", which is incorporated herein by reference, discloses various embodiments of an introducer for positioning an expandable endovascular prosthesis in a lumen of a patient.

Some prosthetic devices may have shorter bare wire stents or bare wire stents that comprise thinner wire. Smaller wire diameter causes the stent to have a lower radial force while in a hollow retention device, and allow more free space for stent struts to move relative to each other. This lower radial force and increased free movement of the stent struts may allow barbs as well as stent eyelets to catch adjacent stent struts and become entangled. It may be desirable to provide a method and apparatus to deploy a graft prosthesis that provides a controlled release of a proximal bare wire stent of the prosthesis that decreases the likelihood of entanglement.

A control mechanism, such as a trigger wire, may prevent a graft prosthesis having a proximal bare wire stent from being released prematurely from a proximal retention device of an introducer. Many introducers utilize a single connection point to retain the graft prosthesis in the retention device. This single-point connection may allow the bare wire stent of the graft prosthesis to rotate within the retention device, which could cause the struts of a bare wire stent to tangle. It may be desirable to keep the bare wire stent from rotating within the retention device to lessen the likelihood of entanglement.

SUMMARY

An introducer for an expandable endovascular prosthesis having a self-expanding stent includes a proximal prosthesis positioning mechanism that has a retention device to retain the self-expanding stent and a control member to selectively release the retention device from the prosthesis. The retention device includes an opening to a cavity that may have a width which tapers from the opening inward. The control member may include a plurality of loops coupled to the prosthesis and a trigger wire. The trigger wire may pass through a first aperture of the retention device, through the plurality of loops, and through and a second aperture of the retention device to retain the loops between the trigger wire and the retention device.

The cavity of the retention device may have a linear, circular, or a parabolic cross section. The cavity may taper so that the maximum width is at least 5% to 10% greater than the minimum width. The introducer may also include a control arrangement for controlling the length of the prosthesis. Additionally, the introducer may include a rotational control arrangement by which the relative angular orientation of the proximal and distal portions of the prosthesis can be adjusted.

A method for placing a prosthesis into an internal lumen using an insertion assembly may include inserting the insertion assembly with the prosthesis into the internal lumen and withdrawing a sheath from the insertion assembly to expose the prosthesis. A stent of the prosthesis may be retained in a retention device with a plurality of loops coupled to the prosthesis and a trigger wire that passes through a first aperture of the retention device, through the plurality of loops, and through a second aperture of the retention device to retain the loops between the trigger wire and the retention device. The method may include removing the trigger wire and moving the retention device proximally away from the prosthesis to release the stent. The method may also include replacing the sheath onto the insertion assembly and retracting the insertion assembly.

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

Figure 1:
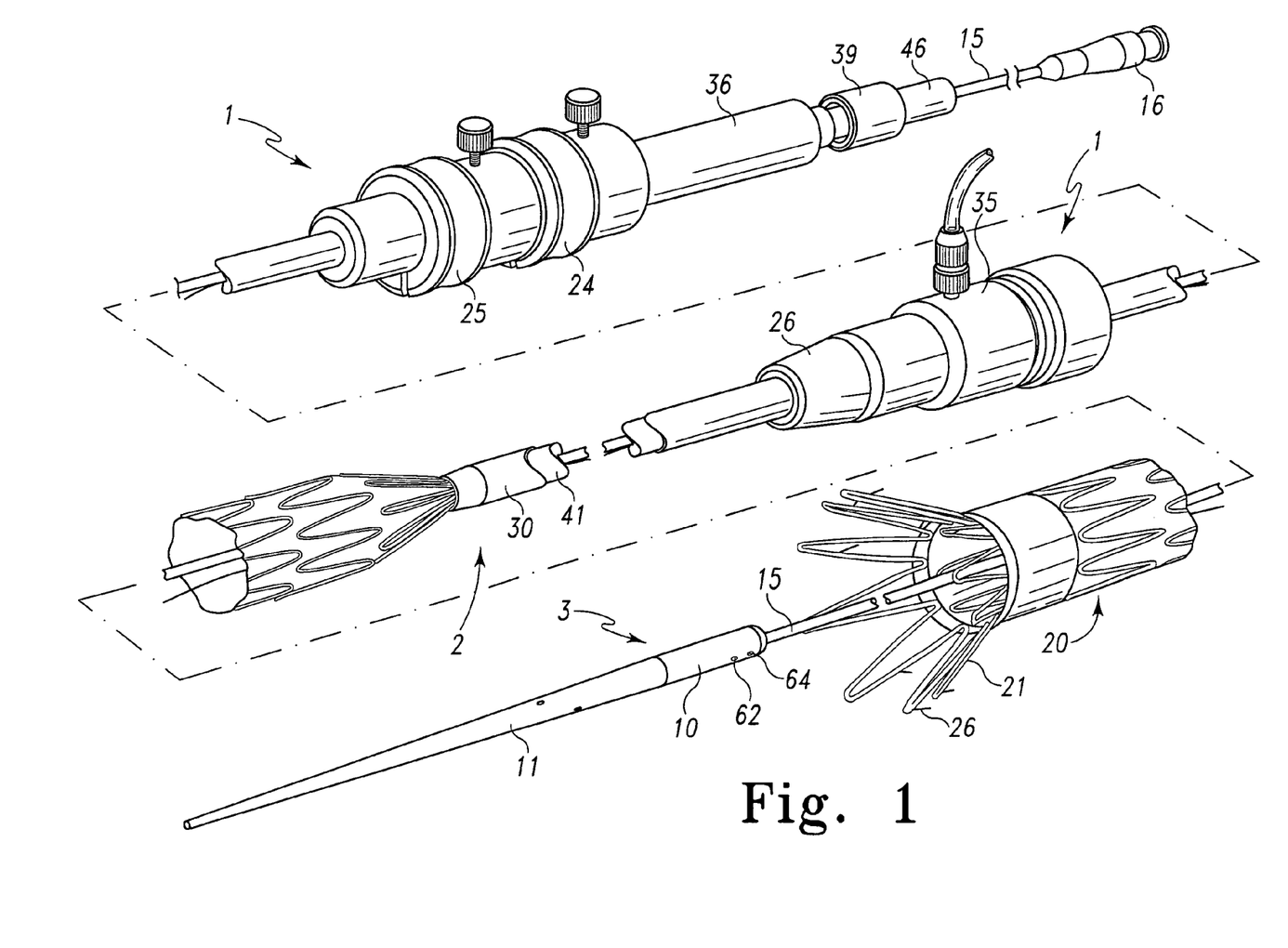
FIG. 1 is a perspective view of selected segments of an introducer of the present invention with a prosthesis partially deployed.

FIG. 1 shows a prosthesis 20, and an endovascular deployment system, also known as an introducer, for deploying the prosthesis 20 in a lumen of a patient during a medical procedure. The introducer includes an external manipulation section 1, a distal positioning mechanism or attachment region 2 and a proximal positioning mechanism or attachment region 3. During a medical procedure to deploy the prosthesis 20, the distal and proximal attachment regions 2 and 3 will travel through the lumen to a desired deployment site. The external manipulation section 1, which is acted upon by a user to manipulate the introducer, remains outside of the patient throughout the procedure.

Figure 2:
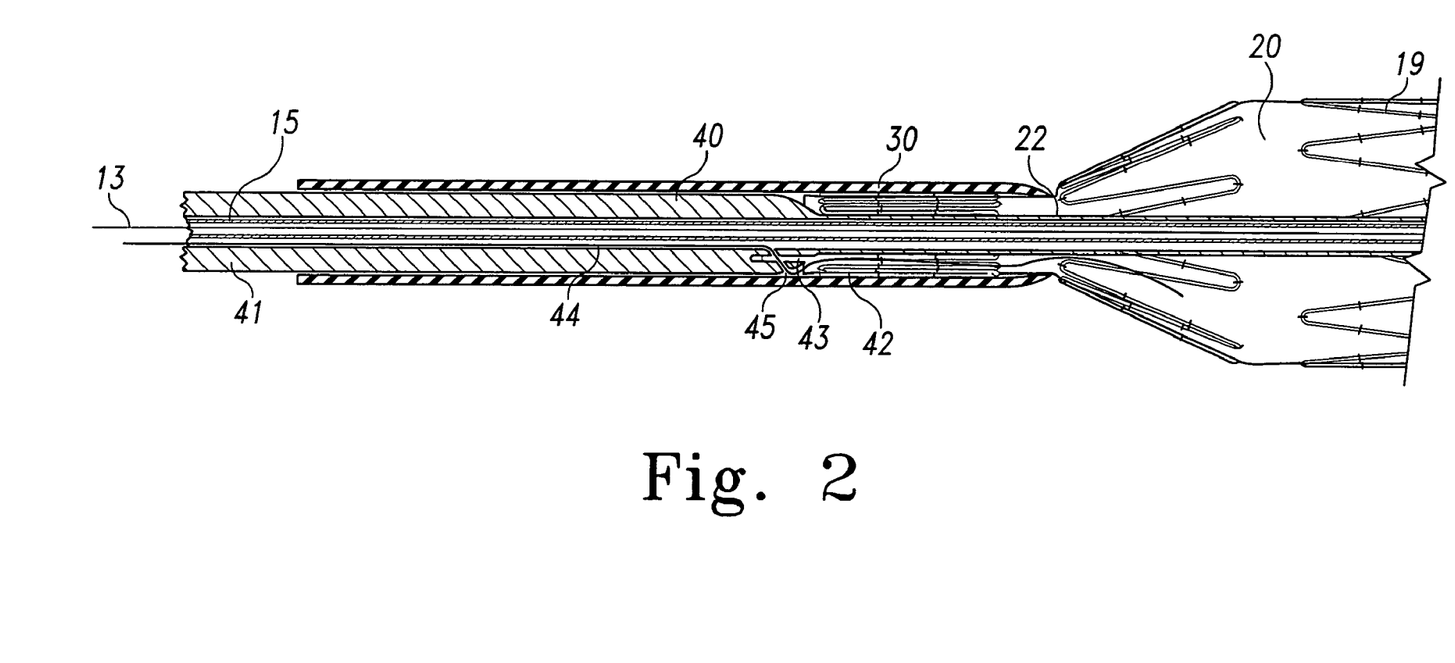
FIG. 2 is a sectional detail view of a portion of the introducer around the distal end of the prosthesis.
Figure 3:
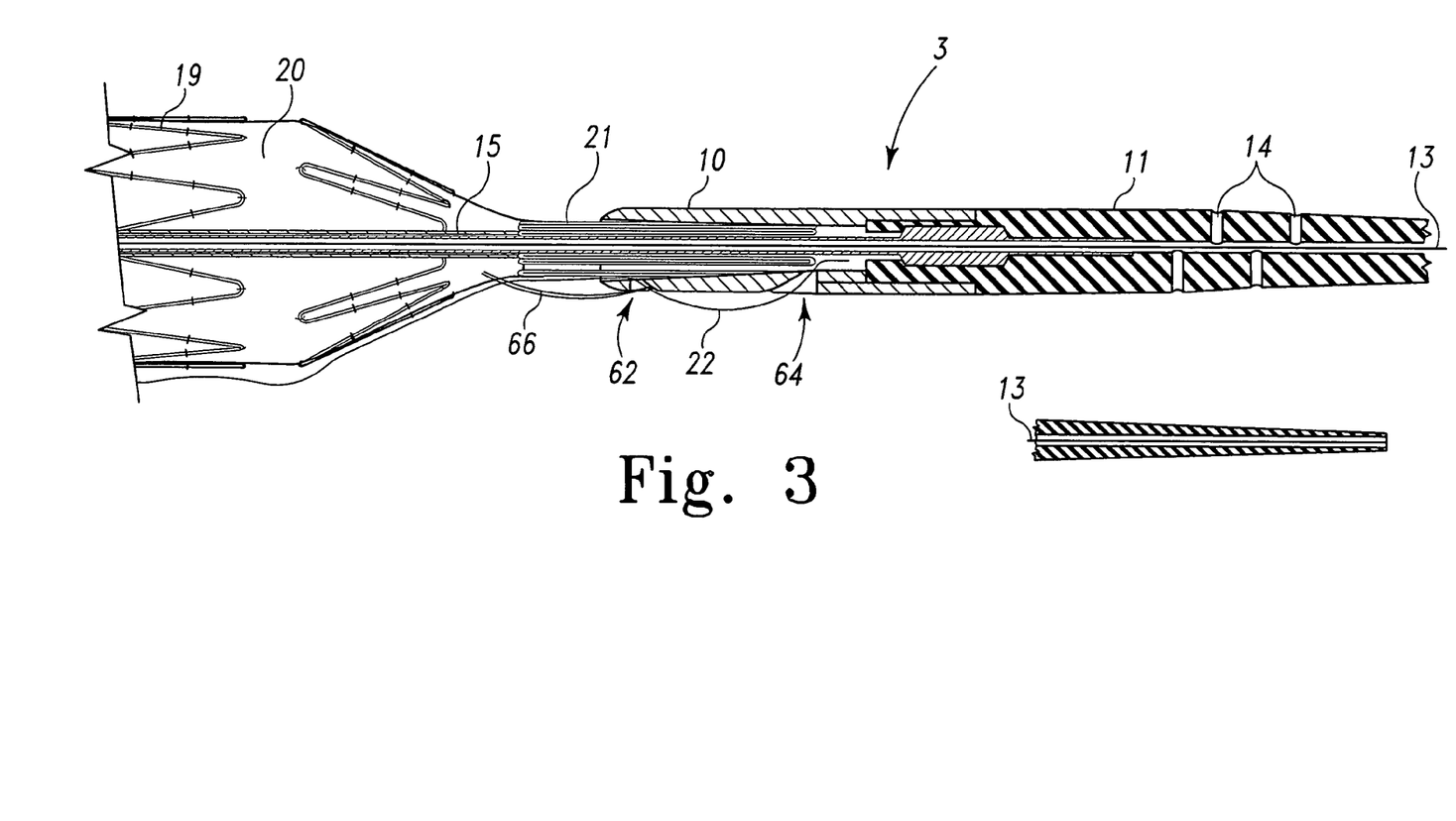
FIG. 3 is a sectional detail view of a portion of the introducer around the proximal end of the prosthesis.

The prosthesis 20 can comprise a tubular graft material, such as Dacron, with self-expanding stents 19 attached thereto as shown in FIGS. 2 and 3. The self-expanding stents 19 cause the prosthesis 20 to expand following its release from the introducer. The prosthesis 20 also includes an exposed self-expanding zigzag stent 21 shown in FIGS. 1 and 3, which is a bare wire stent having barbs 26 that extend from the stent proximal end. When the self-expanding stent 21 is released, the barbs 26 anchor the proximal end of the prosthesis 20 to the surrounding lumen, not shown.

FIG. 3 shows the proximal attachment region 3 in greater detail. The proximal attachment region 3 includes a retention device 10. The retention device 10 has at its proximal end a long tapered flexible extension 11. The flexible extension 11 has an internal longitudinal aperture 12. The longitudinal aperture 12 facilitates advancement of the tapered flexible extension 11 along a previously inserted insertion wire 13. The longitudinal aperture 12 also provides a channel for the introduction of medical reagents. For example, it may be desirable to supply a contrast agent to allow angiography to be performed during placement and deployment phases of the medical procedure.

A thin walled tube 15 generally made of metal is fastened to the extension 11. The thin walled tube 15 is flexible so that the introducer can be advanced within a relatively tortuous vessel, such as a femoral artery. The thin walled tube also allows manipulation longitudinally and rotationally of the proximal attachment region 3. The thin walled tube 15 extends through the introducer to the manipulation section 1, terminating at a connection means 16, as shown in FIG. 7.

Figure 7:
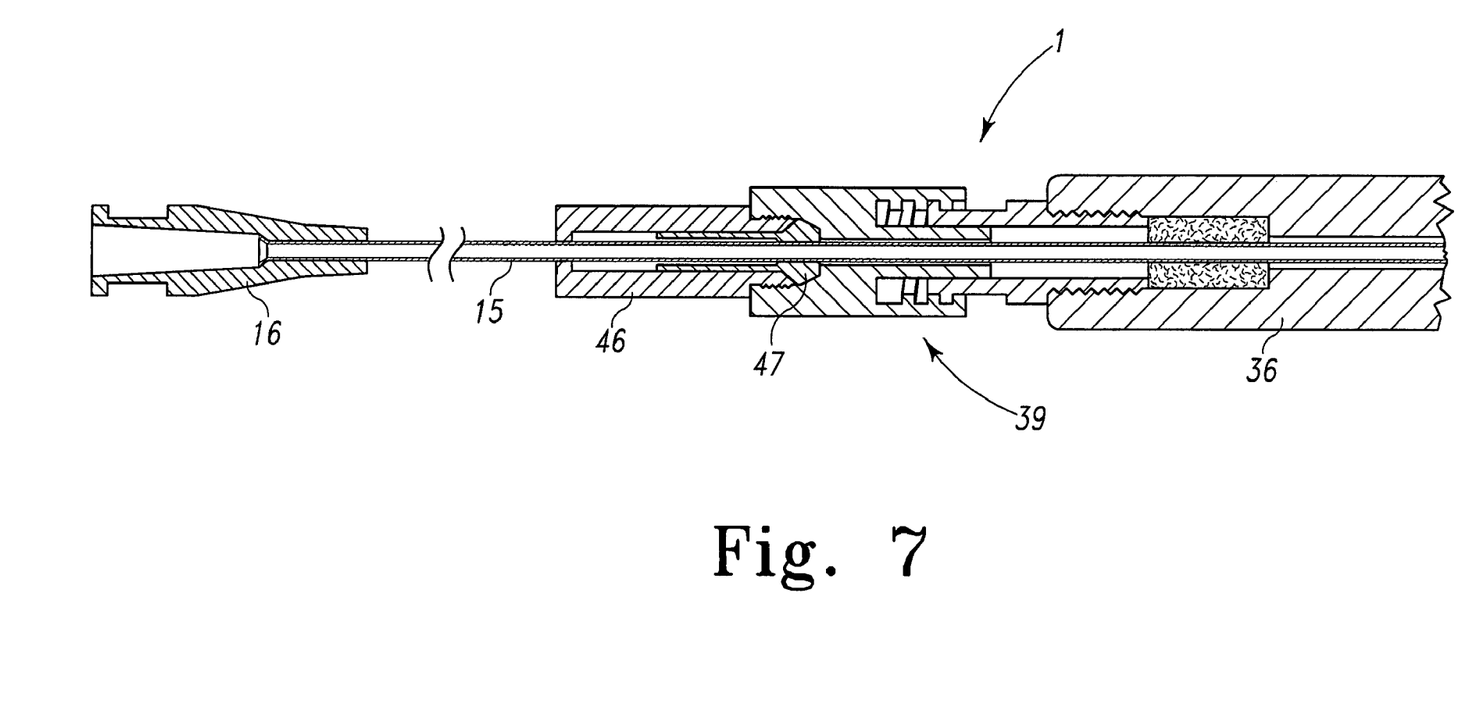
FIG. 7 is a sectional view of a portion of the introducer around the pin vise clamp and the medical reagent introduction tube.

Regarding the introduction of reagents, FIG. 7 shows that the connection means 16 is adapted to accept a syringe to facilitate the introduction of reagents into the metal tube 15.

The metal tube 15 is in fluid communication with the aperture 12 of the flexible extension 11. Therefore, reagents introduced into connection means 16 can flow through the aperture 12 and can emanate from the lateral apertures 14.

As shown in FIG. 2, a tube 41, which can be made of plastic, is coaxial with and radially outside the thin walled tube 15. The tube 41 is "thick walled", which is to say the thickness of the wall of tube 41 is several times that of the thin walled tube 15. Preferably, the tube 41 is five or more times thicker than the thin walled tube 15. A sheath 30 is coaxial with and radially outside the thick walled tube 41. The thick walled tube 41 and the sheath 30 extend distally to the manipulation region 1, as shown in FIG. 5.

FIGS. 2 and 3 illustrate distal and proximal retention and release mechanisms of the introducer, respectively. During the placement phase of the medical procedure, the prosthesis 20 is retained in a compressed condition by the sheath 30. The sheath 30 extends distally to a gripping and haemostatic sealing means 35 of the external manipulation section 1, shown in FIG. 5.

Figure 5:
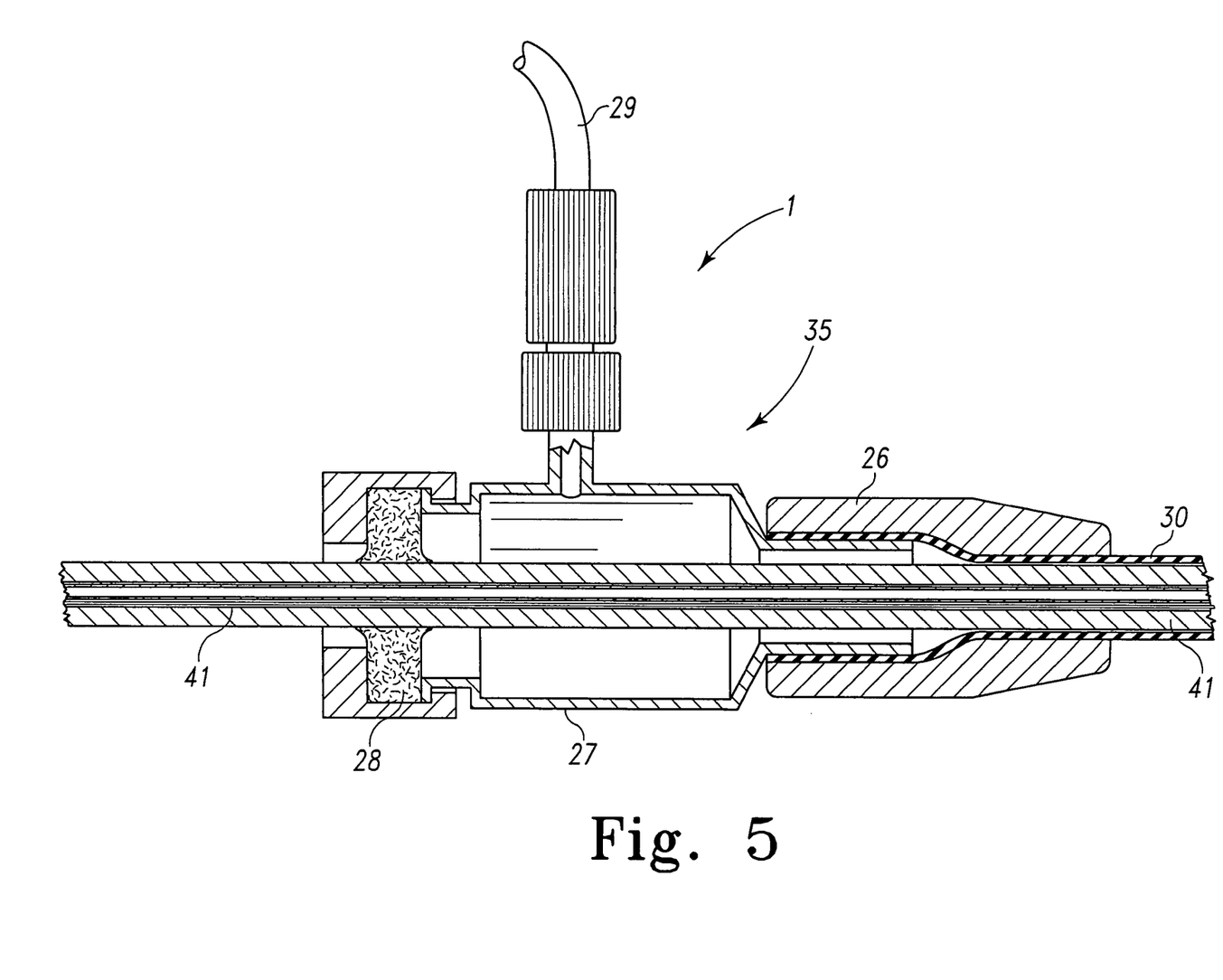
FIG. 5 is a sectional view of a portion of the introducer around the haemostatic seal.

FIG. 5 shows the haemostatic sealing means 35 of the external manipulation section 1 shown in greater detail. The haemostatic sealing means 35 can include a haemostatic seal 27 a side tube 29. The haemostatic seal 27 can also include a clamping collar 26 that clamps the sheath 30 to the haemostatic seal 27. The haemostatic seal 27 can also include a silicone seal ring 28. The silicone seal ring 28 forms a haemostatic seal around the thick walled tube 41. The side tube 29 facilitates the introduction of medical reagents between the thick walled tube 41 and the sheath 30.

During assembly of the introducer, the sheath 30 is advanced over the retention device 10 of the proximal attachment region 3 while the prosthesis 20 is held in a compressed state by an external force. When the prosthesis 20 is in a compressed condition, the proximal self-expanding zigzag stent 21 is retained in the retention device 10 by suture loops 66 and a proximal trigger wire 22 shown in FIG. 3.

Figure 4:
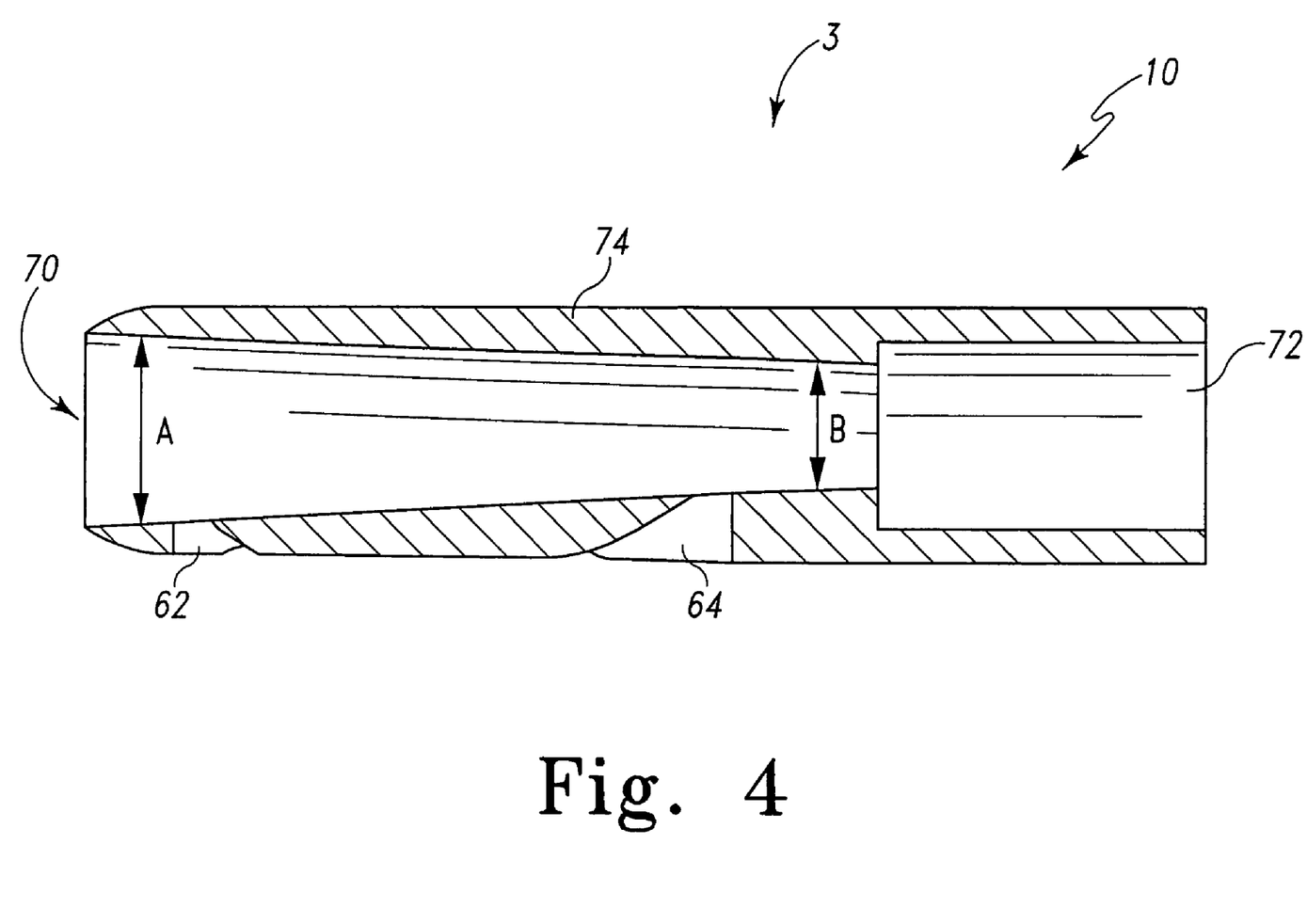
FIG. 4 is a sectional view of a proximal retention device of the introducer.

FIG. 4 shows a detailed cross section of the retention device 10. The retention device 10 includes apertures 62 and 64 to accommodate the proximal trigger wire 22. The retention device 10 includes an opening that extends longitudinally to form the surface of a conical cavity 70, rather than a straight cavity as is the case with some proximal retention devices. The conical cavity 70 decreases in diameter from a maximum diameter A near the distal opening to a minimum diameter B near the proximal end. The conical cavity 70 is shown decreasing as a straight line, but could also decrease as a parabola or some other shape. Preferably, the maximum diameter A is between about 5% and about 20% greater than the minimum diameter B. The conical shape of the cavity 70 forces the struts of the self-expanding stent 21 closer together, and decreases the amount of free space in the cavity 70. Because the struts of the stent 21 are harder pressed against the walls of the cavity 70, and because there is less free space in the cavity 70, the struts of the stent 21 are less likely to move and tangle.

Figure 4A:
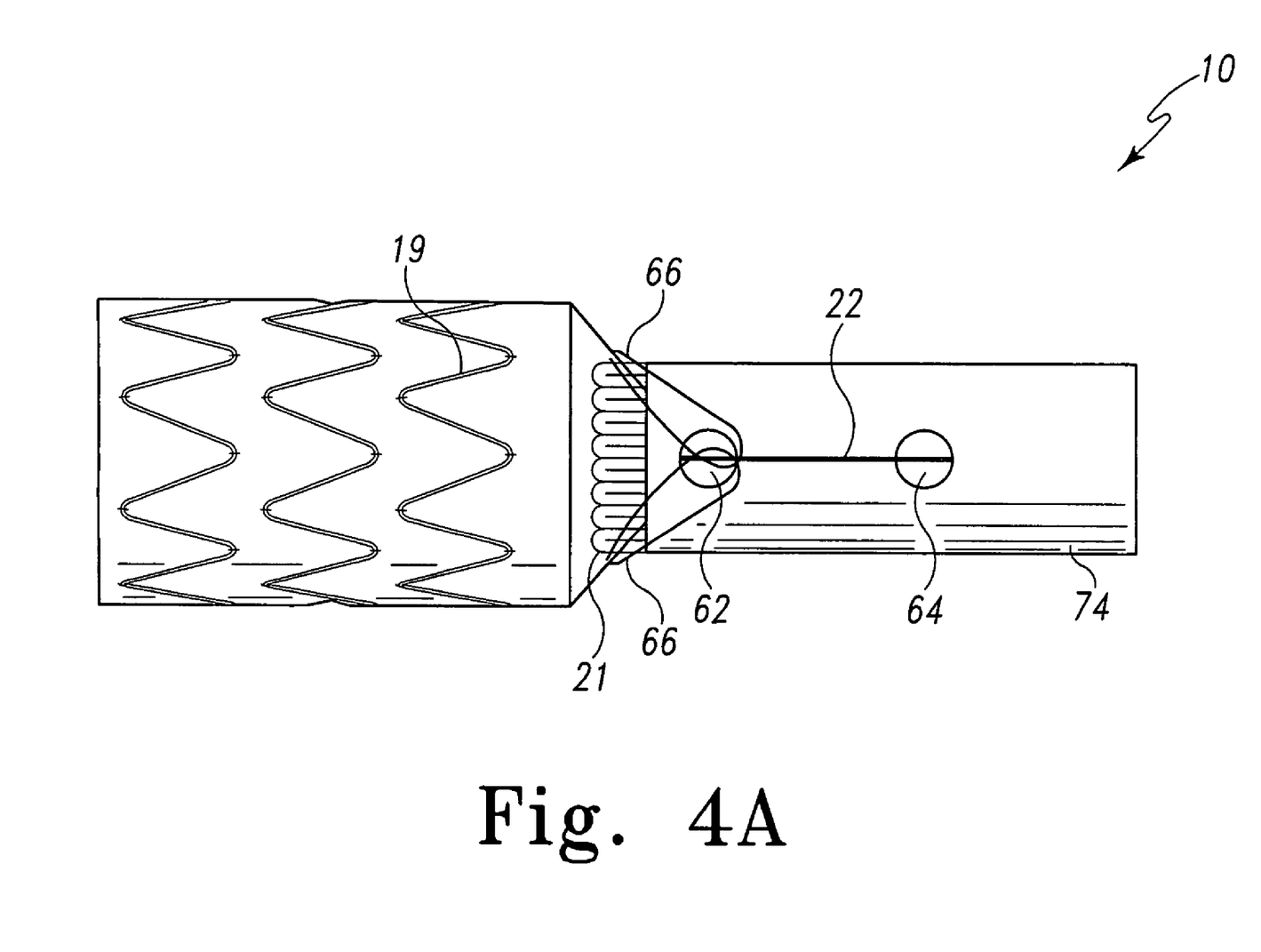
FIG. 4a is a plan view of the proximal retention device of the introducer.

FIG. 4A is a plan view of the retention device 10 showing the prosthesis 20 partially deployed, with the self-expanding zigzag stent 21 still retained in a compressed state. The suture loops 66, shown in detail in FIG. 4A, are coupled to the body of the prosthesis 20, and hold the self-expanding zigzag stent 21 in the retention device 10 until the trigger wire 22 is removed. While the trigger wire 22 is in place, the suture loops 66 prevent the retention device 10 and the prosthesis 20 from separating. The trigger wire 22 retains the suture loops 66 between itself and an outer surface of the retention device 10.

The suture loops 66 are attached to opposing sides of the prosthesis 20, for example separated by 90 to 180 degrees. Since the suture loops 66 do not stretch, they provide opposing torques that prevent the prosthesis 20 from rotating. When the trigger wire 22 is removed, the suture loops 66 are free to move, and the retention device 10 may be released from the self-expanding zigzag stent 21. This configuration differs from introducers that have a single point of attachment securing a bare wire self-expanding zigzag stent in a retention device, which may allow the stent to rotate within the retention device and lead to entanglement of the stent's struts.

Figure 6:
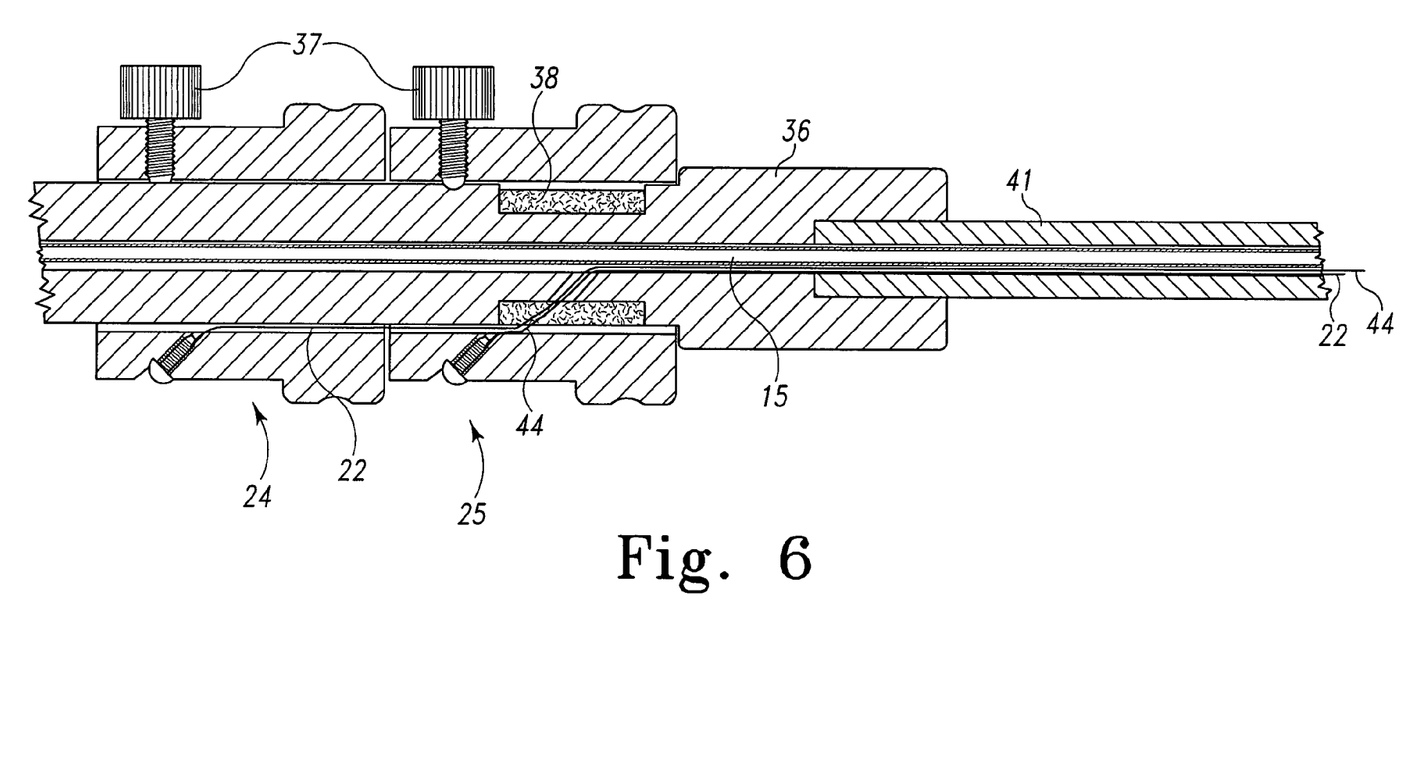
FIG. 6 is a sectional view of a portion of the introducer around the trigger wire release mechanism.

As shown in FIG. 6, the proximal trigger wire 22 extends through the annular space between the thick walled tube 41 and the thin walled tube 15 to the manipulation region 1. The proximal trigger wire 22 exits the annular space at a proximal wire release mechanism 24. The self-expanding stent 21 is released by retracting the sheath 30, removing the trigger wire 22, and then sliding the proximal attachment region 3, including the retention device 10, proximally away from the stent 21. Once the retention device 10 has cleared the self-expanding stent 21, the stent 21 will expand. The suture loops 66, the trigger wire 22, and the proximal wire release mechanism 24 form a control member to selectively release the retention device 10 from the prosthesis 20 by holding the self-expanding stent 21 in the retention device 10 until the prosthesis 20 is positioned at a desired site in the lumen.

A distal attachment or retention section 40, as shown in FIG. 2, is coupled to the thick walled tube 41. Alternatively, the distal attachment or retention section 40 may be formed in the thick walled tube 41. The distal attachment section 40 retains a distal end 42 of the prosthesis 20 during the procedure. The distal end 42 of the prosthesis 20 includes a loop 43. A distal trigger wire 44 extends through the loop 43. The distal trigger wire 44 also extends through an aperture 45 in the distal attachment section 40 and into the annular region between the thin walled tube 15 and the thick walled tube 41.

FIG. 6 shows a proximal portion of the external manipulation section 1. The release wire actuation section has a body 36 that is mounted onto the thick walled plastic tube 41. The thin walled tube 15 passes through the body 36. The distal wire release mechanism 25 is mounted for slidable movement on the body 36. A clamping screw 37 prevents inadvertent early release of the distal end 42 of the prosthesis 20. Similarly, the proximal wire release mechanism 24 is mounted for slidable movement on the body 36. A clamping screw 37 prevents inadvertent early release of the self-expanding zigzag stent 21 of the prosthesis 20.

As shown in FIG. 6, the distal trigger wire 44 extends through the annular space between the thick walled tube 41 and the thin walled tube 15 to the manipulation region 1. The distal trigger wire 44 exits the annular space at a distal wire release mechanism 25. The distal trigger wire 44 and the distal wire release mechanism 25 form a control member to selectively release the distal retention section 40 from the prosthesis 20 when the prosthesis is positioned at a desired site in the lumen.

The positioning of the proximal and distal wire release mechanisms 24 and 25 is such that the proximal wire release mechanism 24 must be moved before the distal wire release mechanism 25 can be moved. Therefore, the distal end 42 of the prosthesis 20 cannot be released until the self-expanding zigzag stent 21 has been released and anchored to the lumen. A haemostatic seal 38 is provided so the release wire 44 can extend out through the body 36 to the release mechanism 25 without unnecessary blood loss during the medical procedure.

FIG. 7 shows a distal portion of the external manipulation section 1. A pin vise 39 is mounted onto the distal end of the body 36. The pin vise 39 has a screw cap 46. When screwed in, the vise jaws 47 clamp against (engage) the thin walled metal tube 15. When the vise jaws 47 are engaged, the thin walled tube 15 can only move with the body 36, and hence the thin walled tube 15 can only move with the thick walled tube 41 (not shown). With the screw cap 46 tightened, the entire assembly, except for the external sleeve 30, can be moved as one.

FIGS. 8 through 13 show the various stages of the deployment of the prosthesis 20 during the medical procedure. A guide wire 13 is introduced, for example, into the femoral artery and advanced until the tip of the guide wire 13 is beyond the region into which the prosthesis 20 is to be deployed.

Figure 8:
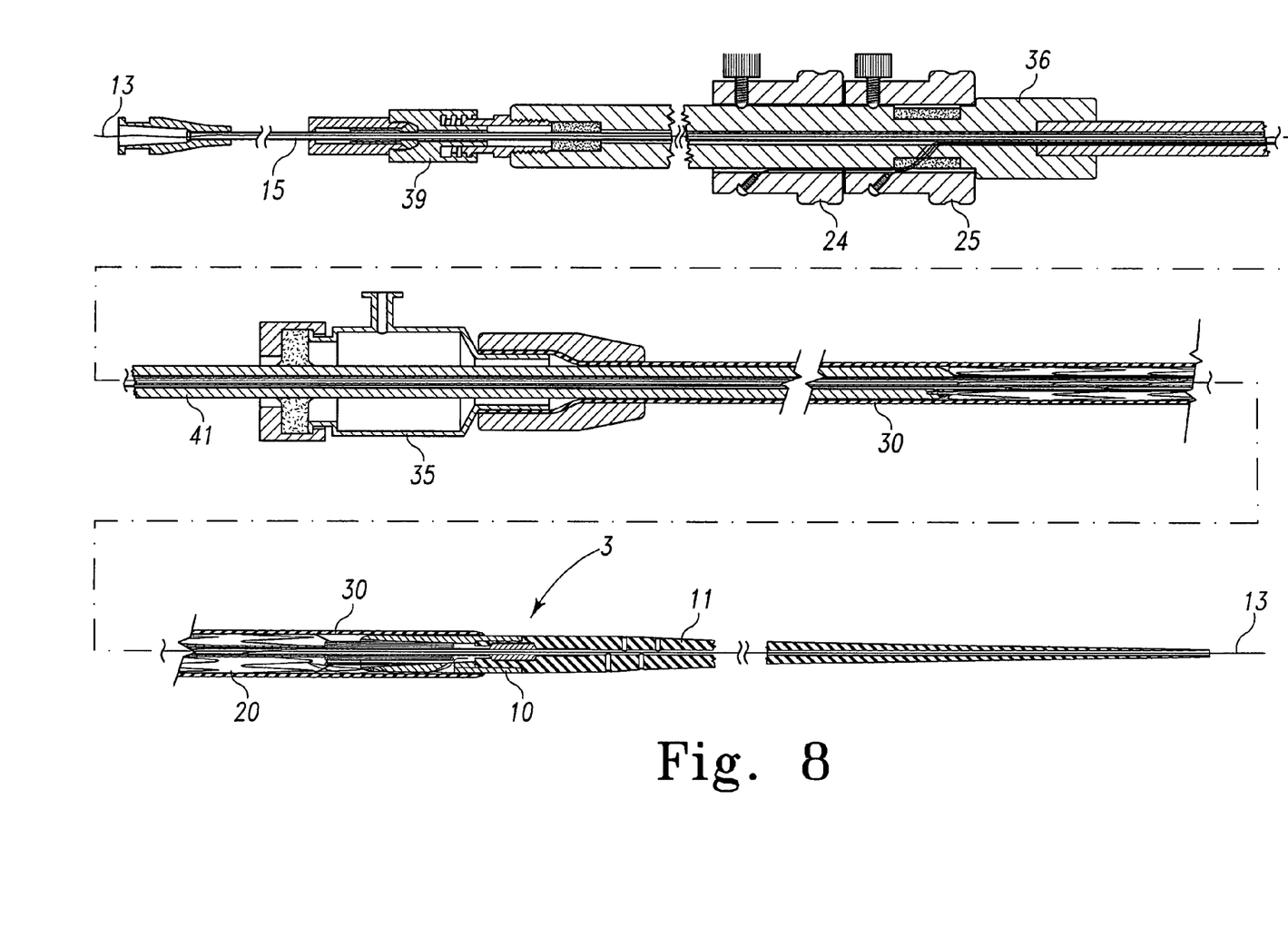
FIG. 8 is a segmented sectional view of the introducer of FIG. 1 fully loaded and ready for introduction into a patient.

In FIG. 8, the introducer assembly is shown fully assembled ready for introduction into a patient. The ends of the prosthesis 20 are retained by the proximal and distal retaining assemblies respectively, while the external sleeve 30 compresses the middle portion of the prosthesis intermediate the ends. If, for example, an aortic aneurism is to be grafted, the introducer assembly can be inserted through a femoral artery over the guide wire 13 as shown in FIG. 8, and positioned by radiographic techniques (not discussed here).

Figure 9:
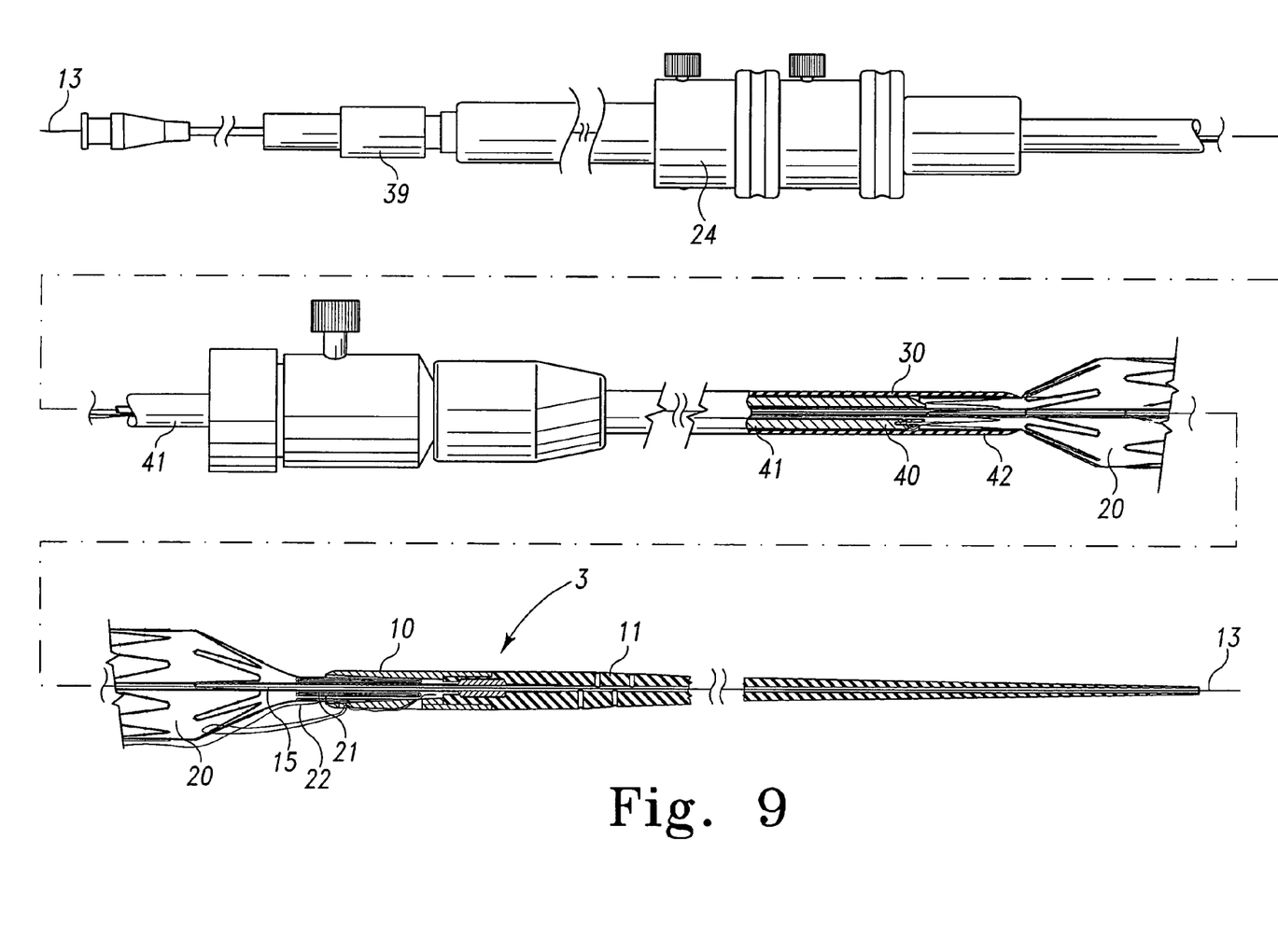
FIG. 9 is a view similar to FIG. 8 showing an initial stage of deployment of the prosthesis.

In FIG. 9, the introducer assembly is in a desired position for deployment of the prosthesis 20. The external sheath 30 is withdrawn to just proximal of the distal attachment section 40. This action releases the middle portion of the prosthesis 20 so that the middle portion can expand radially. The proximal self-expanding stent 21, however, is still retained within the retention device 10. Also, the distal end 42 of the prosthesis 20 is still retained within the external sheath 30.

By release of the pin vise 39 to allow small movements of the thin walled tubing 15 with respect to the thick walled tubing 41, the prosthesis 20 may be lengthened or shortened or rotated or compressed for accurate placement in the desired location within the lumen. X-ray opaque markers (not shown) may be placed along the prosthesis 20 to assist with placement of the prosthesis.

Figure 10:
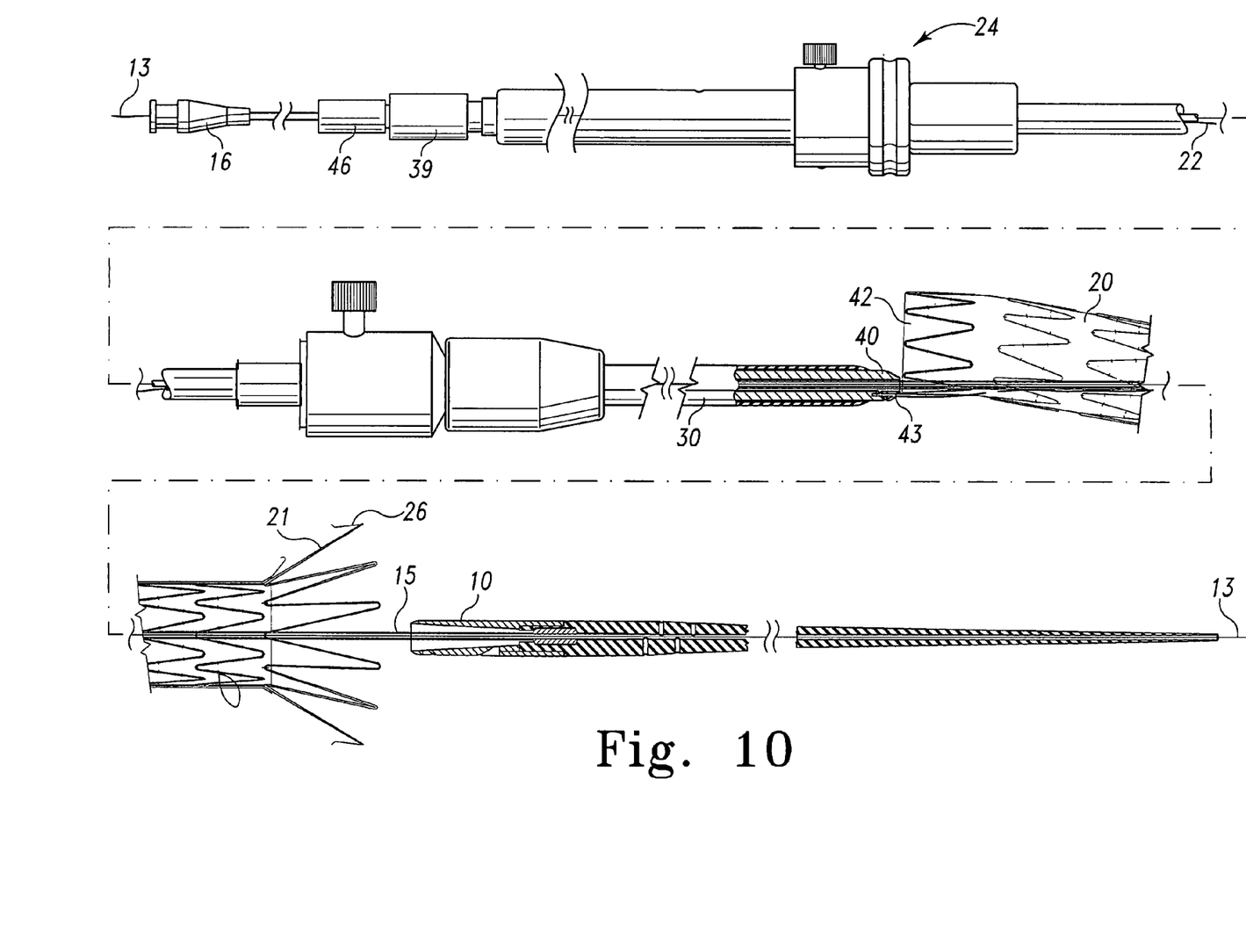
FIG. 10 is a view similar to FIG. 8 showing release of the prosthesis proximal end during deployment.

In FIG. 10, the "proximal" trigger wire 22 has been removed, allowing the retention device 10 to be separated from the self-expanding zigzag stent 21, as explained above. At this stage, the proximal trigger wire release mechanism 24 and the "proximal" trigger wire 22 can be removed completely. Also, the screw cap 46 of the pin vise 39 has been loosened so that the thin walled tubing 15 can be pushed in a proximal direction to move the proximal attachment means 10 in a proximal direction. When the proximal attachment means 10 no longer surrounds the self-expanding stent 21 at the proximal end of the prosthesis 20, the self-expanding stent 21 expands. When the self-expanding stent 21 expands, the hooks or barbs 26 on the self-expanding stent 21 grip into the walls of the lumen to hold the proximal end of the prosthesis 20 in place.

At this point, the distal end 42 of the prosthesis 20 is still retained by the distal attachment means 40, with the loop 43 retained therein. The external sheath 30 is then withdrawn to distal of the distal attachment section 40 to allow the distal end 42 of the prosthesis 20 to expand. At this point, the distal end 42 of the prosthesis 20 may still be moved. Consequently, the prosthesis 20 can still be rotated or lengthened or shortened or otherwise moved for accurate positioning. Where the prosthesis 20 to be deployed is a bifurcated graft, the movement at this stage may ensure that the shorter leg is directed in the direction of the contra-iliac artery.

Figure 11:
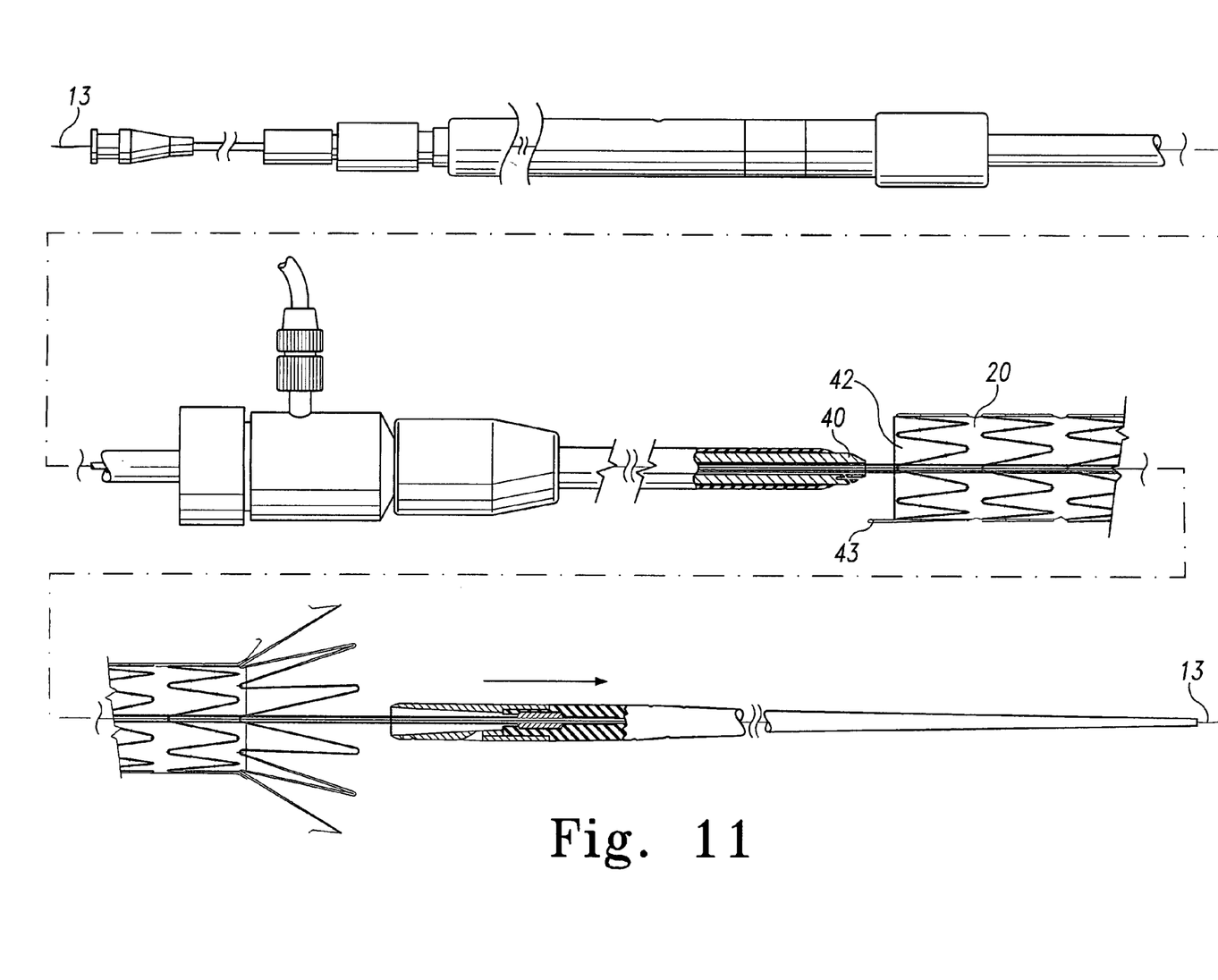
FIG. 11 is a view similar to FIG. 8 showing release of the prosthesis distal end during deployment.

In FIG. 11, the distal end 42 of the prosthesis 20 has been released by removal of the distal trigger wire 44. At this stage, the distal trigger wire release mechanism 25 and the distal trigger wire 44 can be removed completely. This removal may be accomplished by passing the distal wire release mechanism 25 over the pin vise 39 and the connection means 16. The loop 43 of the terminal distal self-expanding zigzag stent 19 is hence released, and the prosthesis 20 is now free to expand to the walls of the vessel. At this point, the introducer is ready to be removed.

Figure 12:
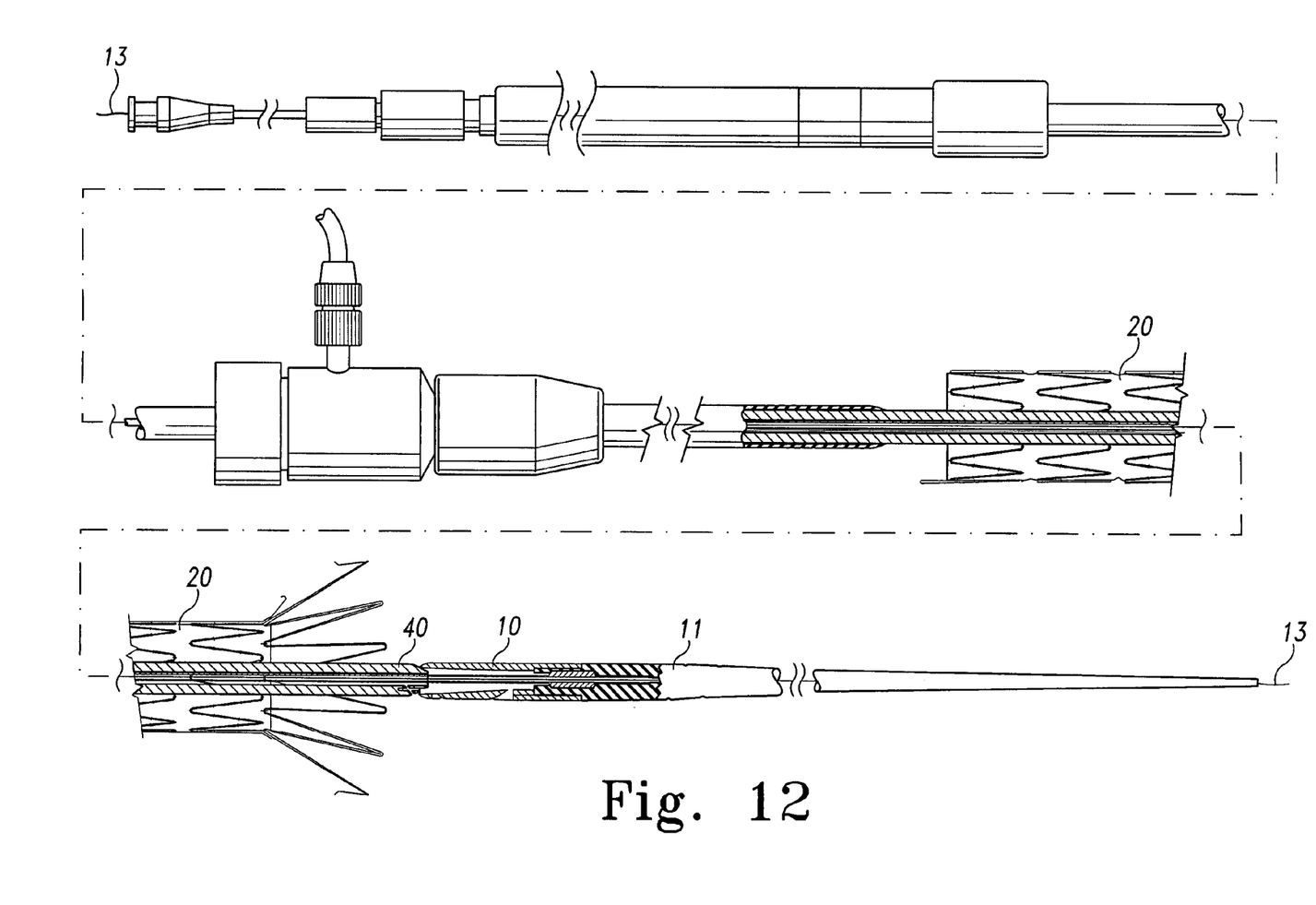
FIG. 12 is a view similar to FIG. 8 showing the advancement of the distal attachment mechanism to the proximal attachment mechanism.

In FIG. 12, the first stage of removal is shown. First, the distal attachment section 40 is advanced until it is received in the rear of the proximal attachment device 10. The proximal attachment device 10, the tapered flexible extension 11, and the distal attachment device 40 are then removed together, as shown in FIG. 12.

Figure 13:
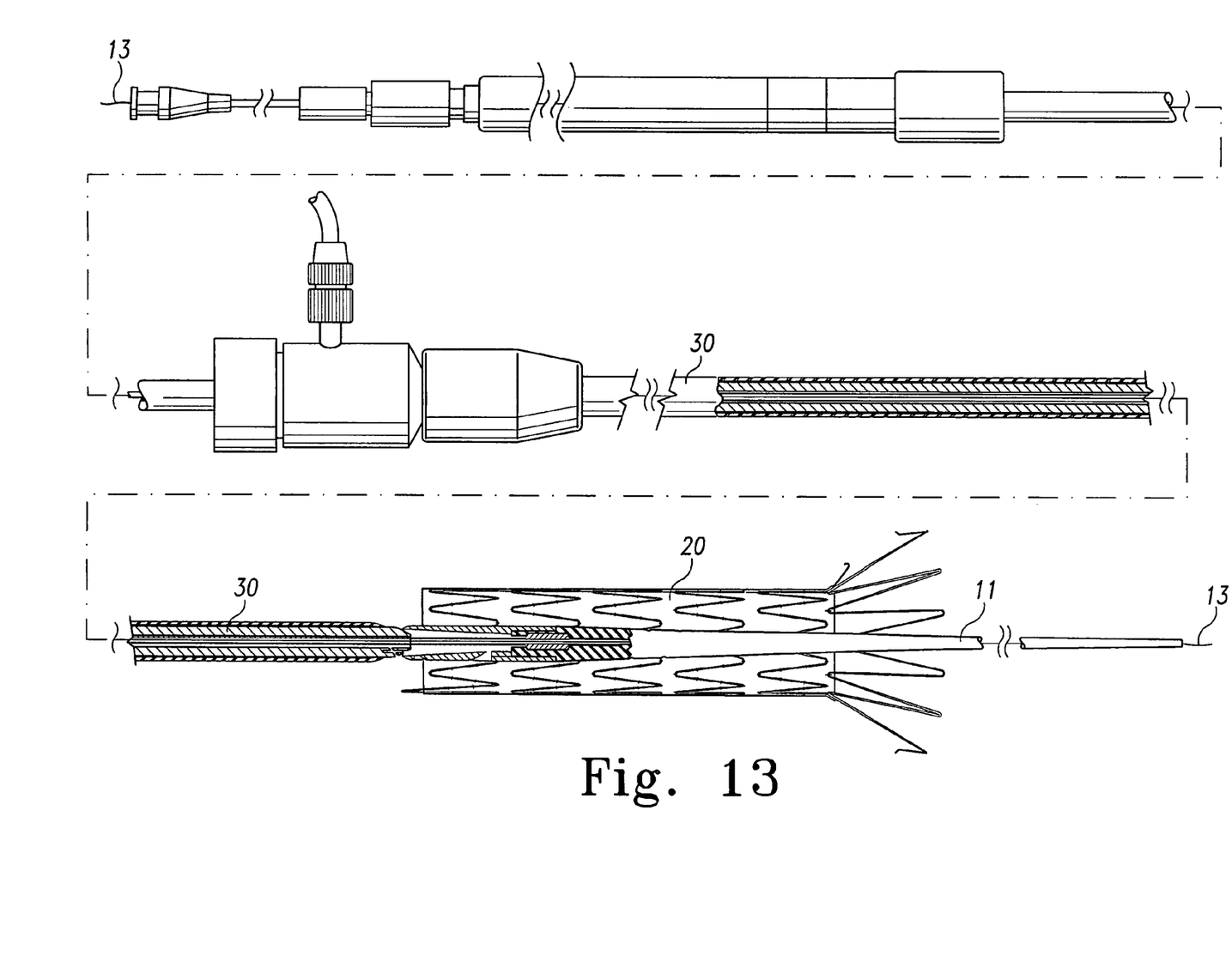
FIG. 13 is a view similar to FIG. 8 showing the withdrawal of the introducer.

In FIG. 13, the sheath 30 has been advanced to uncover the joint between the proximal attachment device 10 and the distal attachment section 40. The sheath 30 may be removed with the proximal attachment device 10, the tapered flexible extension 11 and the distal attachment device 40. Alternatively, these items could be removed separately, followed by removal of the external sleeve 30.

Throughout this specification, unless the context requires otherwise, the words "comprise" and "include" and variations such as "comprising" and "including" will be understood to imply the inclusion of an item or group of items, but not the exclusion of any other item or group items.

While various embodiments of the invention have been described, it will be apparent to those of ordinary skill in the art that many more embodiments and implementations are possible within the scope of the invention. Furthermore, although various indications have been given as to the scope of this invention, the invention is not limited to any one of these but may reside in two or more of these combined together. Accordingly, the invention is not to be restricted except in light of the attached claims and their equivalents.

The invention claimed is:

1. An introducer for an expandable endovascular prosthesis, the introducer comprising:
    an expandable prosthesis having a proximal portion, a distal portion, and self-expanding stent extending from the proximal portion;
    a distal prosthesis positioning mechanism including a distal retention section and a first control member to selectively release the distal retention section from the prosthesis; and
    a proximal prosthesis positioning mechanism including a retention device to retain the self-expanding stent therein and a second control member to selectively release the retention device from the prosthesis;
    wherein the retention device comprises a cylindrical body having a cavity, the cavity including an opening at a distal end of the retention device and a surface extending longitudinally therefrom to form the surface of the cavity, the cavity having a first width at the opening and a second width at a longitudinal distance along the surface from the opening, the first width being greater than the second width, where spacing between struts of the self-expanding stent is decreased longitudinally along the surface of the cavity from the opening.

2. The introducer of claim 1, wherein the cavity surface has a linear cross section.

3. The introducer of claim 1, wherein the cavity surface has a parabolic cross section.

4. The introducer of claim 1, wherein the cavity surface has a circular cross section.

5. The introducer of claim 1, wherein the first width of the cavity is at least five percent greater than the second width.

6. The introducer of claim 1, wherein the first width of the cavity is at least ten percent greater than the second width.

7. The introducer of claim 1, further comprising a control arrangement for controlling the length of the prosthesis.

8. The introducer of claim 1, further comprising a rotational control arrangement by which the relative angular orientation of the proximal and distal portions of the prosthesis can be adjusted, wherein said introducer further comprises a tapered flexible extension extending longitudinally from a proximal end of the retention device.

9. The introducer of claim 1, wherein the retention device comprises a first side aperture and a second side aperture, and the second control member includes a plurality of loops coupled to the prosthesis and a trigger wire that passes through the first side aperture of the retention device, through the plurality of loops, and through the second side aperture of the retention device to retain the loops between the trigger wire and the retention device.

10. An introducer for an expandable endovascular prosthesis having a proximal portion, a distal portion, and self-expanding stent, the introducer comprising:
 a control section to be maintained external to the patient;
 a proximal prosthesis positioning mechanism including a retention device to retain the self-expanding stent until the prosthesis is positioned at a desired site in a lumen, the retention device having a first side aperture and a second side aperture; and
 a rotation control member comprising a plurality of loops separated by an angle in a range of at least 30 to 180 degrees and coupled to the prosthesis and a trigger wire coupled to the rotation control section that passes through the first side aperture of the retention device, through the plurality of loops, and through the second side aperture of the retention device to retain the loops between the trigger wire and the retention device to inhibit rotation of the self-expanding stent within the retention device until the prosthesis is suitably positioned.

11. The introducer of claim 10, wherein the loops comprise suture material.

12. The introducer of claim 10, wherein a cross-section of the prosthesis is circular, and the loops are separated by an angle of at least about 30 degrees.

13. The introducer of claim 10, wherein a cross-section of the prosthesis is circular, and the loops are separated by an angle of at least about 60 degrees.

14. The introducer of claim 10, wherein a cross-section of the prosthesis is circular, and the loops are separated by an angle of at least about 90 degrees.

15. The introducer of claim 10, wherein a cross-section of the prosthesis is circular, and the loops are separated by an angle of at least about 120 degrees.

16. The introducer of claim 10, further comprising a control arrangement for controlling a deployed length of the prosthesis.

17. The introducer of claim 10, further comprising a rotational control arrangement by which the relative angular orientation of the proximal and distal portions of the prosthesis can be adjusted.

18. The introducer of claim 10, further comprising a distal prosthesis positioning mechanism coupled between the control section and the proximal prosthesis positioning mechanism.

19. The introducer of claim 10, wherein the distal prosthesis positioning mechanism includes a distal attachment section, the control section comprises a tube, and the distal attachment section is coupled to the tube.

20. An introducer for an expandable endovascular prosthesis, the introducer comprising:
 an expandable prosthesis having a proximal portion, a distal portion, and self-expanding stent extending from the proximal portion;
 a distal prosthesis positioning mechanism including a distal retention section and a first control member to selectively release the distal retention section from the prosthesis; and
 a proximal prosthesis positioning mechanism including a retention device to retain the self-expanding stent therein and a second control member to selectively release the retention device from the prosthesis, the retention device having a first side aperture and a second side aperture;
 wherein the retention device comprises a cylindrical body having a cavity, the cavity including an opening at a distal end of the retention device and a surface extending longitudinally therefrom to form the surface of the cavity, the cavity having a first width at the opening and a second width at a longitudinal distance along the surface from the opening, the first width being greater than the second width, where spacing between struts of the self-expanding stent is decreased longitudinally along the surface of the cavity from the opening.

* * * * *